United States Patent
Hare et al.

(10) Patent No.: US 7,290,547 B2
(45) Date of Patent: *Nov. 6, 2007

(54) COVERING FOR AN ASEPTIC TREATMENT SITE

(76) Inventors: Joseph Hare, 953 E. 43rd Ave., Spokan, WA (US) 99203; Judson E. Threlkeld, 19503 NE. 6th, Camas, WA (US) 98607

( * ) Notice: Subject to any disclaimer, the term of this patent is extended or adjusted under 35 U.S.C. 154(b) by 620 days.

This patent is subject to a terminal disclaimer.

(21) Appl. No.: 10/726,324

(22) Filed: Dec. 1, 2003

(65) Prior Publication Data

US 2005/0115570 A1   Jun. 2, 2005

(51) Int. Cl.
  *A61B 19/00* (2006.01)
  *A61B 19/08* (2006.01)
(52) U.S. Cl. ............... 128/854; 128/849; 128/853
(58) Field of Classification Search ........... 128/853, 128/854, 897, 849, 888; 602/41–59; 225/39–42
  See application file for complete search history.

(56) References Cited

U.S. PATENT DOCUMENTS

| | | | |
|---|---|---|---|
| 3,799,161 A | 3/1974 | Collins | |
| 3,826,253 A | 7/1974 | Larsh et al. | |
| 3,916,887 A | 11/1975 | Kelly | |
| 4,027,665 A | 6/1977 | Scrivens | |
| 4,378,794 A | 4/1983 | Collins | |
| 4,414,968 A | 11/1983 | Amin | |
| 4,433,026 A | 2/1984 | Molde | |
| 4,462,396 A | 7/1984 | Wichman | |
| 4,471,769 A | 9/1984 | Lockhart | |
| 4,690,137 A | 9/1987 | Starzmann | |
| 5,151,314 A | 9/1992 | Brown | |
| 5,161,544 A | 11/1992 | Morris | |
| 5,197,493 A * | 3/1993 | Grier-Idris | 128/853 |
| 5,225,236 A * | 7/1993 | Keusch et al. | 428/77 |
| 5,372,589 A | 12/1994 | Davis | |
| 5,445,165 A | 8/1995 | Fenwick | |
| 5,538,012 A * | 7/1996 | Wiedner et al. | 128/853 |
| 5,562,107 A * | 10/1996 | Lavender et al. | 128/888 |
| 5,702,356 A * | 12/1997 | Hathman | 602/41 |
| 5,975,082 A * | 11/1999 | Dowdy | 128/849 |
| 6,105,579 A | 8/2000 | Levitt et al. | |
| 6,357,445 B1 | 3/2002 | Shaw | |
| 6,382,212 B1 | 5/2002 | Borchard | |
| 6,530,376 B1 | 3/2003 | Padget et al. | |
| 6,564,803 B2 | 5/2003 | Lofgren | |
| 2002/0108615 A1 * | 8/2002 | Levitt et al. | 128/853 |
| 2003/0009122 A1 * | 1/2003 | Veras | 602/42 |
| 2003/0113827 A1 * | 6/2003 | Burkoth | 435/14 |
| 2003/0121522 A1 | 7/2003 | Gingles et al. | |
| 2006/0207609 A1 * | 9/2006 | Gil et al. | 128/849 |

FOREIGN PATENT DOCUMENTS

| | | |
|---|---|---|
| GB | 2326100 | 12/1998 |
| WO | WO 2005/053754 | 6/2005 |

* cited by examiner

*Primary Examiner*—Patricia Bianco
*Assistant Examiner*—Brandon Jackson
(74) *Attorney, Agent, or Firm*—Withers & Keys, LLC

(57) ABSTRACT

A covering for an aseptic treatment site is described and which includes a substrate defining an aperture which permits selective access to an aseptic treatment site on a patient; and a transparent cover is borne by the substrate and which is removably affixed in substantially aseptic covering relation relative to the aperture.

29 Claims, 4 Drawing Sheets

COVERING FOR AN ASEPTIC TREATMENT SITE

TECHNICAL FIELD

The present invention relates to a covering for an aseptic treatment site, and more specifically to a fenestrated surgical drape which has a portion that may remain in place after a surgical intervention and which will permit a clinician to continually observe and access, if necessary, the aseptic treatment site.

BACKGROUND OF THE INVENTION

The prior art is replete with numerous examples of surgical drapes which have been designed and utilized, through the years, to aid clinicians in the treatment of patients having various maladies. Typically, such surgical drapes have been adapted for use with a wide variety of electronic and mechanical devices which are used for treating the patient's medical conditions. Depending on the nature of the condition, such medical devices, can for example, be surgically implanted, connected externally to the patient receiving treatment, or even used during a surgical technique.

Fenestrated surgical drapes have been used, heretofore, to maintain sterile conditions, maintain patient privacy, absorb bodily fluids, and further provide a clear and clean work area for the clinician. The prior art surgical drapes, such as the one shown in FIG. 1 employ a fenestration or opening in the surgical drape which provides the clinician with access to the desired site on the patient's body while preserving the function of the surgical drape which is utilized to cover other areas of the patient's body.

In a typical utilization of such fenestrated surgical drapes, a medical treatment site, such as a surgical site is located, and thereafter the site is prepared for surgery by making it substantially aseptic. Thereafter, the surgical drape having the fenestration is placed over the surgical site and the medical procedure or surgery is initiated. Following completion of the surgery, the typical practice is to remove the entire surgical drape because portions of the drape may have absorbed body fluid during the surgery. The patient is then moved from the surgical theater to a recovery room. Some surgical procedures require that the surgical site be monitored for a period of time in order to detect any abnormalities in the recovery of the patient. On some occasions, irregularities may occur either at the surgical site, or elsewhere in the patients' body which indicate that the previous surgical procedure has been unsuccessful or another situation has arisen in the patient's body which indicates that further surgical intervention is required by the clinician. In these circumstances, immediate surgical intervention is not possible inasmuch as the original surgical site is no longer in an aseptic condition. Consequently under these conditions, the surgical site must be again rendered aseptic before a clinician can gain access to same. This time delay to render a surgical site aseptic can be significant, and may under some circumstances be life threatening.

Therefore, a covering for an aseptic treatment site which addresses the perceived shortcomings of the prior art practices and devices utilized heretofore is the subject matter of the present application.

SUMMARY OF THE INVENTION

A first aspect of the present invention relates to a covering for an aseptic treatment site which includes, a substrate defining an aperture which permits selective access to an aseptic treatment site on a patient; and a transparent cover borne by the substrate and which is removably affixed in substantially aseptic covering relation relative to the aperture.

Another aspect of the present invention relates to a covering for an aseptic treatment site which includes, a flexible substrate having opposite first and second surfaces, and which defines an aperture which permits access to an aseptic treatment site on a patient; a first adhesive region borne on the second surface of the flexible substrate, and which substantially surrounds the aperture; a flexible transparent cover moveably affixed on the first surface of the flexible substrate, and which is moveable along a course of travel between a first, covering position relative to the aperture, and which permits observation of the aseptic treatment site, to a second, uncovered position relative to the aperture, and which permits access to the aseptic treatment site; and a second adhesive region borne by the flexible, transparent cover, and which releasably adhesively affixes the flexible transparent cover to the first surface of the flexible substrate.

Yet another aspect of the present invention relates to a covering for an aseptic treatment site which includes, a flexible substrate having a first region, and a releasably detachable second region, and wherein the first region defines an aperture which permits access to an aseptic treatment site on a patient; a first adhesive region substantially surrounding the aperture, and which is borne by the first region, and wherein the first adhesive region releasably adhesively affixes the first region on the body of the patient in an orientation such that the first region surrounds the aseptic treatment site; a flexible transparent cover hingedly affixed on the first surface of the flexible substrate, and wherein the transparent cover has a peripheral edge, opposite first and second surfaces, and opposite first and second ends, and wherein the second end of the flexible transparent cover is hingedly affixed on the first surface, and wherein the first end is moveable along a substantially arcuately shaped path of travel between a first position, wherein the transparent cover is disposed in a covering relation relative to the aperture and substantially out of direct contact with the aseptic treatment site, to a second position, wherein the transparent cover is disposed in an orientation which allows access to the aseptic treatment site by way of the aperture; and a second adhesive region disposed on either one of the transparent cover or the substrate and which releaseably adhesively affixes the peripheral edge of the transparent cover on the substrate and in the first covering position relative to the aperture, and wherein the second adhesive region releases the transparent cover from the first position when force is applied to the first end of the transparent cover, and wherein the second adhesive region permits the transparent cover to be repeatedly moved between the first and second positions without substantially adhesively detaching the first adhesive region from the patient.

These and other aspects of the present invention will be discussed in greater detail hereinafter.

BRIEF DESCRIPTION OF THE DRAWINGS

The accompanying drawings serve to explain the principles of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
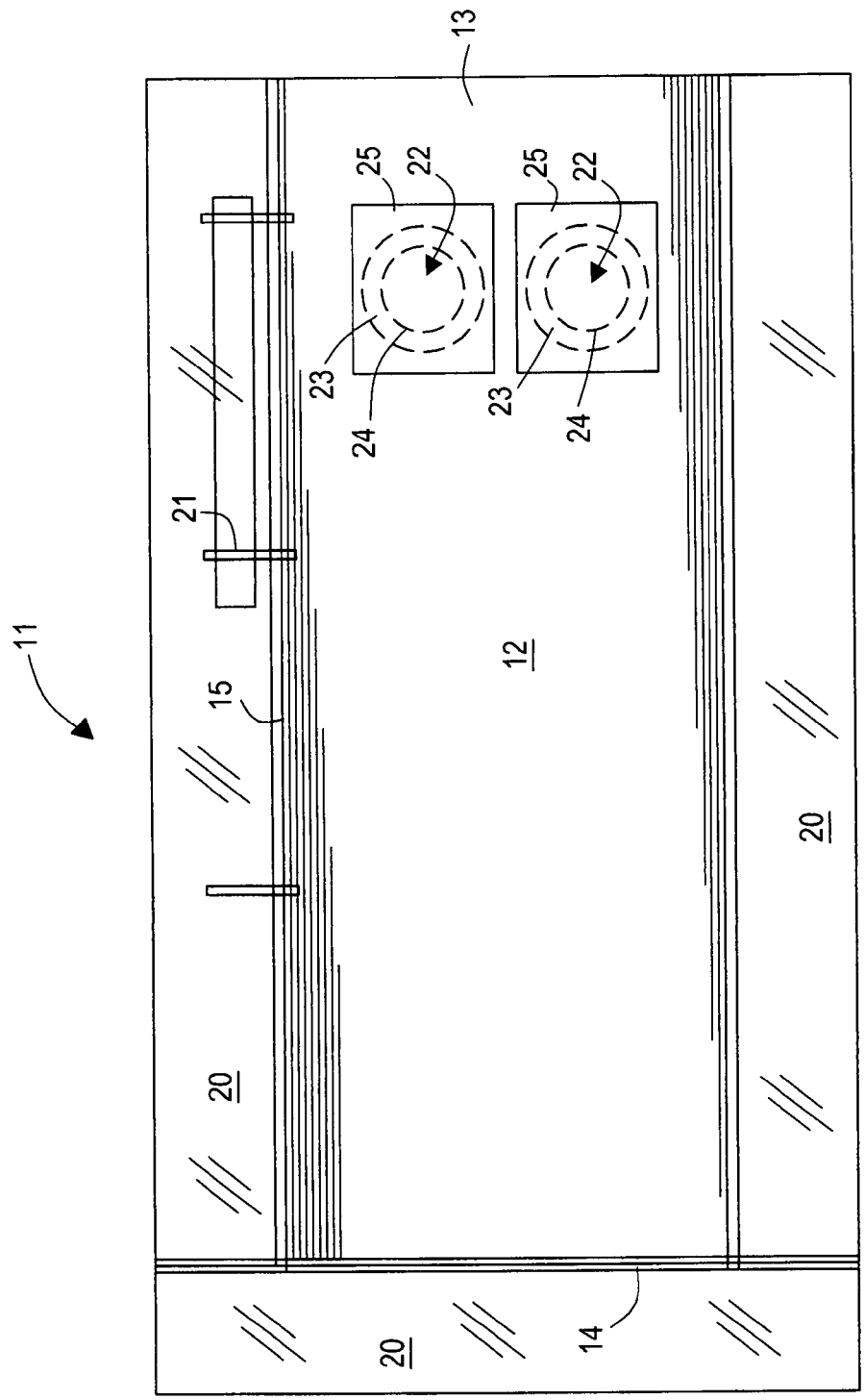
FIG. 1 is a bottom plan view of a prior art surgical drape.
Figure 2:
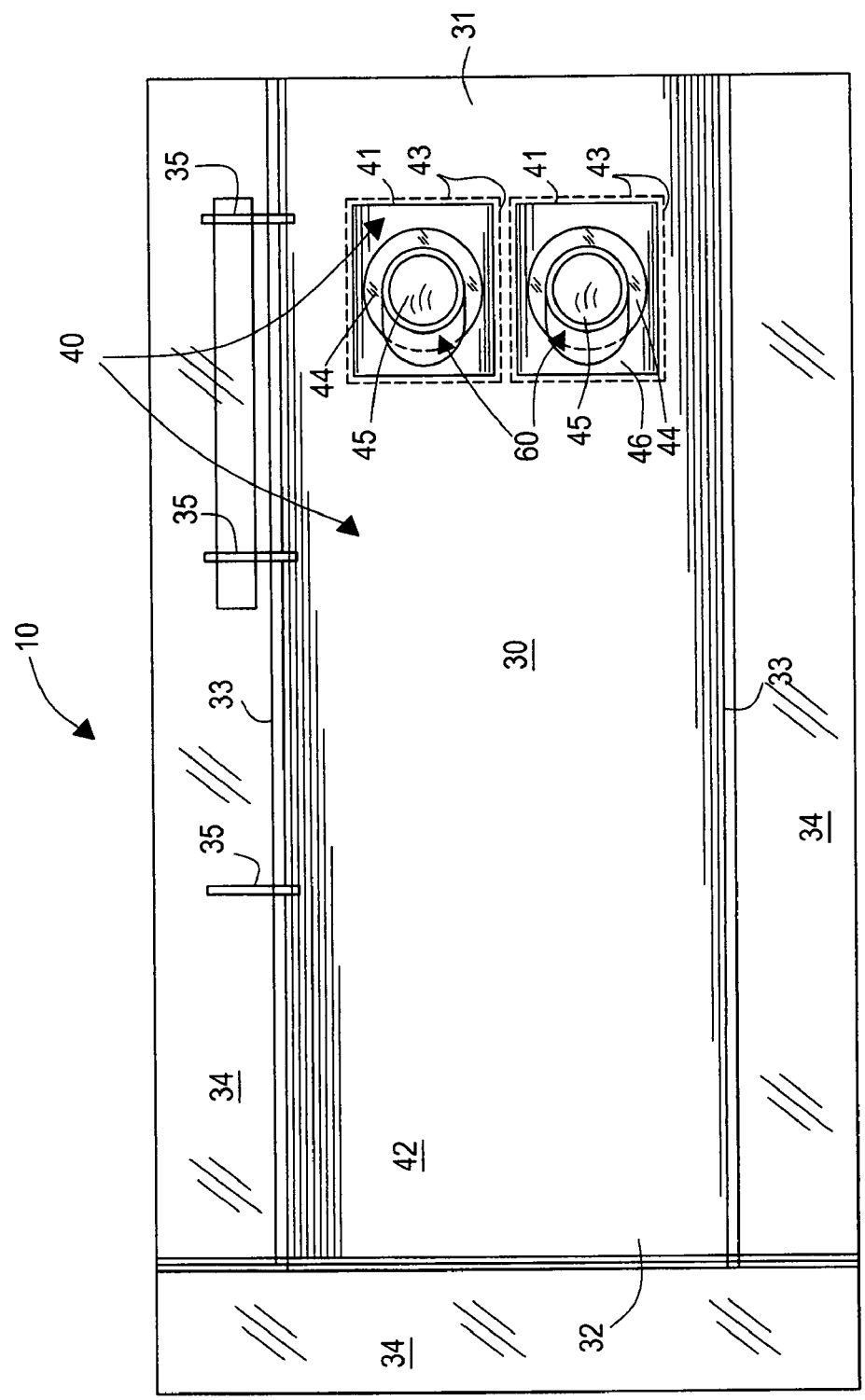
FIG. 2 is a top plan view of the covering for an aseptic treatment site of the present invention.

The covering for an aseptic treatment site of the present invention is generally indicated by the numeral 10 in FIG. 2 and following. Referring as a first matter to FIG. 1, a prior art, commercially available angiography drape is shown therein and is designated by the numeral 11. The prior art drape 11 includes a main body 12, which is typically fabricated, at least in part, from a cellulosic substantially opaque material. The main body 12 has a first end 13, which is typically oriented towards the head of a patient, and an opposite second end 14, which is positioned near the feet of the patient. The main body 12 is defined by a peripheral edge 15. A transparent pliable perimeter portion 20 is provided, which is attached to peripheral edge 15. This perimeter portion 20 includes a plurality of deformable attachment members 21, which are adhesively affixed to the pliable perimeter portion 20 and which can be deformed in order to secure perimeter portion 20 to an adjacent object such as an examination table. These deformable attachment members 21 are bent or otherwise deformed in order to attach perimeter portion 20 to the object, thereby securing drape 11 in an orientation such that it is secured out of the way of the clinician and other healthcare workers working adjacent thereto. The main body 12 includes a pair of windows, apertures or fenestrations 22, which are formed in predetermined positions near first end 13, and which provide a convenient location whereby a clinician may gain access to a patient's body positioned below surgical drape 11 in order to perform medical procedures. As should be understood, windows, apertures or fenestrations 22 formed in main body 12 are occluded, in part, by a flexible transparent adhesive border 23, which is affixed to main body 12 and which defines an aperture 24 through which the clinician will gain access to the patient's body. A release paper of conventional design 25 is releasably positioned in covering relation relative to flexible transparent adhesive border 23. This release paper 25 is removable, thereby exposing adhesive border 23 therebelow. Thereafter, the clinician positions aperture 24 in an appropriate orientation and flexible transparent adhesive border 23 secures main body 12 in place such that it does not move during the medical procedure.

Referring now to FIG. 2, the covering for an aseptic treatment site of the present invention and which is designated by the numeral 10 is shown in a top plan view. As seen in FIG. 2 and following, the invention includes a main body 30 which is fabricated, at least in part, from a cellulosic substrate which is substantially opaque. The main body 30 provides an aseptic barrier and is also capable of absorbing body or other fluids which might be generated during a surgical or other medical procedure. The main body 30 has a first end 31 which is typically oriented at the head of a patient, (not shown) and a second end 32 which is oriented typically at or toward the feet of a patient. The main body 30 is defined by a peripheral edge 33. Similar to the prior art device shown in FIG. 1, a transparent pliable perimeter portion 34 is provided. This perimeter portion also includes deformable attachment members 35 which operate in a fashion similar to that described with respect to the prior art device shown in FIG. 1.

Figure 6:
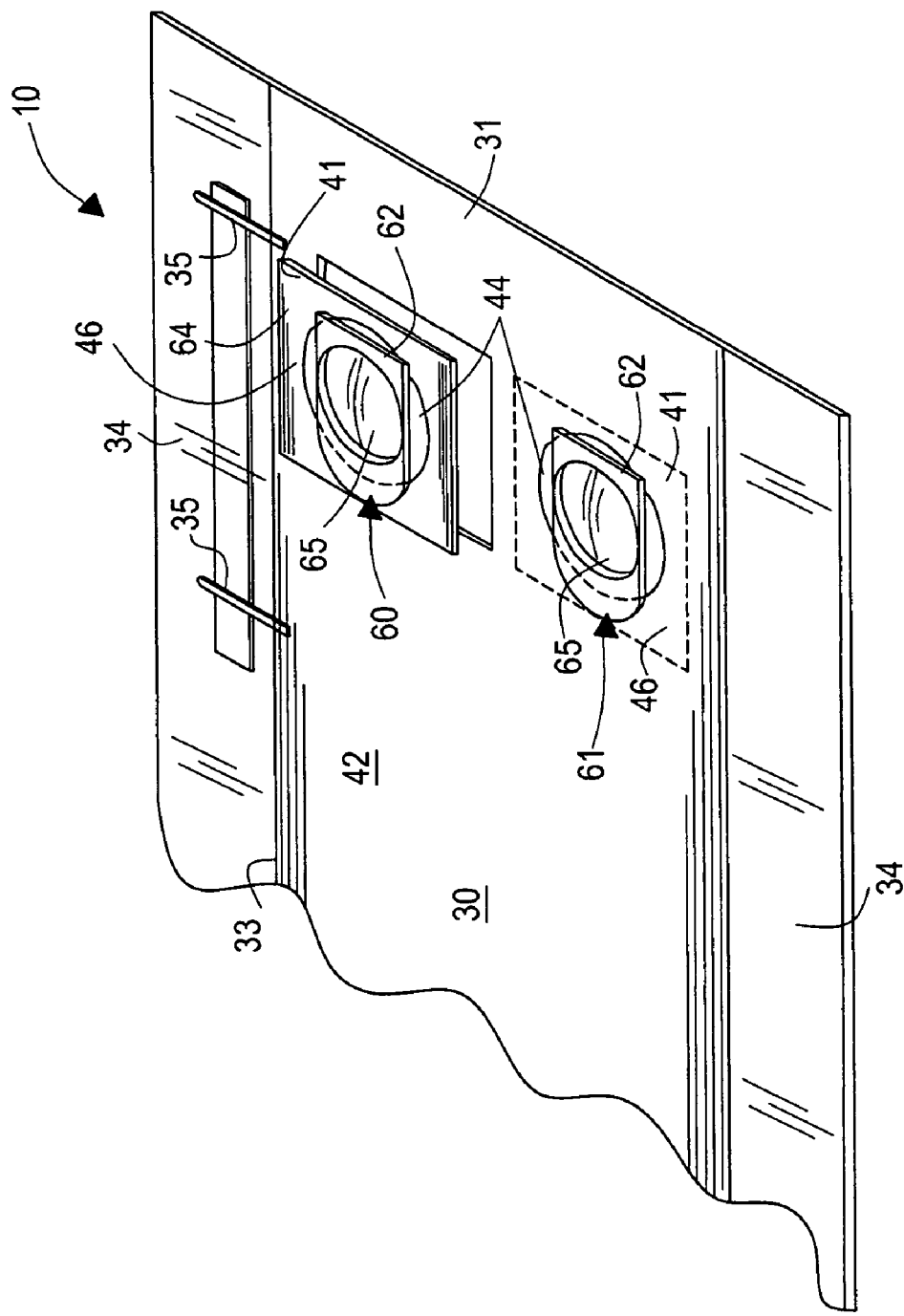
FIG. 6 is a fragmentary, perspective, view of the covering for an aseptic treatment site with one portion detached.

Referring still to FIGS. 2 and 6, the present invention 10 includes a pair of regions generally indicated by the numeral 40. The pair of regions includes a first region 41 and a selectively detachable second region 42 which is joined to the first region. As seen in FIG. 2 and following, the selectively detachable second region comprises a preponderance of the main body 30. A plurality of perforations or weakened areas 43 are formed in a pattern in the second region 42 and which surround, at least in part, the first region 41. As will be appreciated from the discussion which follows, this plurality of weakened areas or other perforations further facilitate the detachment of the second region 42 from the first region 41. As noted above, the main body 30 is typically fabricated, at least in part, from a cellulosic substrate, and the plurality of perforations or weakened areas which define a periphery of the first region, permits the second region to be removed from the first region by tearing the main body along the perforations. The first region 41 includes a first portion 44 which defines an aperture 45; and a second portion 46 which is made integral with the first portion. As seen in FIG. 2 and following, the second region 42 is selectively detachable relative to the second portion 46. As should be understood, the second region 42 and the second portion 46 may be fabricated from the same material, or from different materials as the needs require. Yet further, the first and second portions 44 and 46 may be fabricated from the same materials or from different materials depending upon the construction and end use of same.

Figure 3:
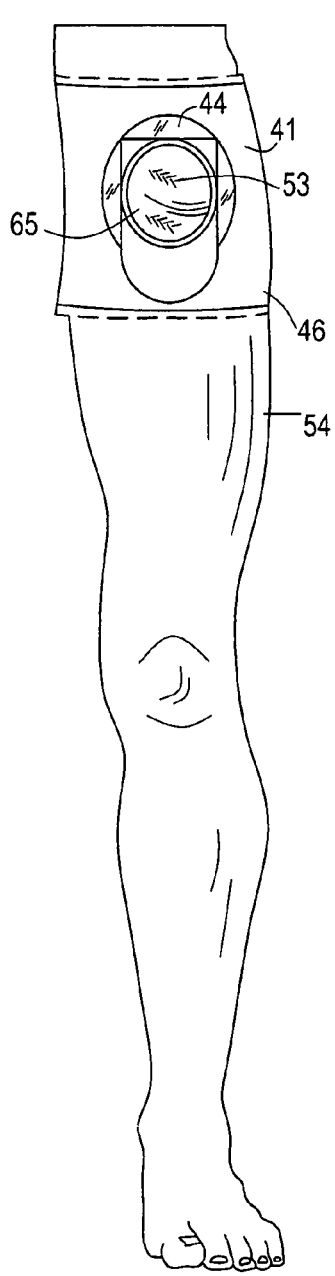
FIG. 3 is a partial, fragmentary top plan view of the covering for an aseptic treatment shown positioned on a patient's limb.
Figure 4:
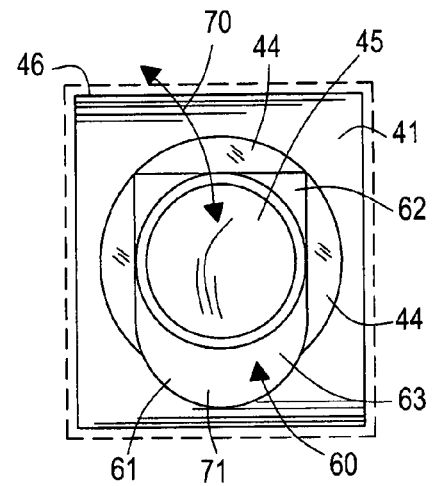
FIG. 4 is a fragmentary, somewhat enlarged, top plan view of the covering for an aseptic treatment site with a transparent cover shown in a covered position.
Figure 5:
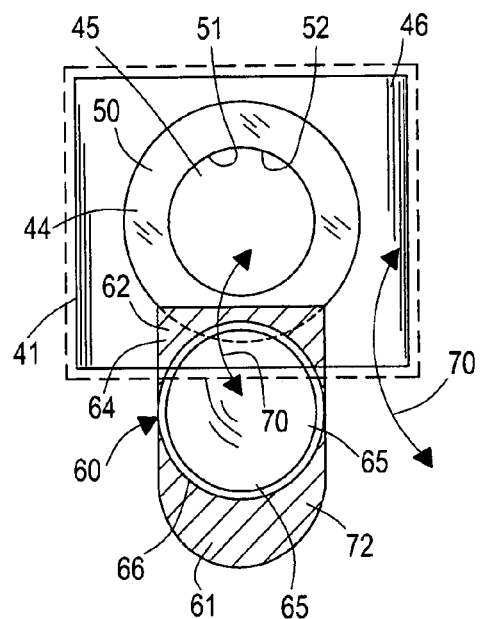
FIG. 5 is a fragmentary, top plan view of the covering for an aseptic treatment site with a transparent cover mounted on same shown in an uncovered position.

The first portion 44 which defines the aperture 45 has a first surface 50 and an opposite second surface 51 (FIG. 5). The second surface 51 has an adhesive coating 52 applied thereto. The adhesive coating 52 is operable to adhere the first portion 44 to a patient's body and in a given position such that it surrounds a surgical or medical intervention site 53 as seen in FIG. 3. The adhesive coating 52 has a predetermined adhesive strength. This surgical intervention site 53 may be on a limb 54 as shown in FIG. 3, or on the torso of a patient (not shown). As seen in FIG. 2 and following, the present invention 10 includes a transparent cover 60 which is moveably borne by the first portion 44, and which is removably affixed in a substantially aseptic covering relation relative to the aperture 45 (FIGS. 3 and 4). In particular, it will be seen from a study of FIGS. 4 and 5 that the transparent cover 60 is hingedly mounted on the first portion 44. The transparent cover 60 has a first end 61 which may be grasped by a clinician, and an opposite second end 62 which is hingedly mounted to the first portion 44. Still further, the transparent cover includes a first surface 63 and an opposite second surface 64. The transparent cover defines a cavity 65 which, when the cover is placed in an appropriate orientation in covering relation relative to the aperture 45, ensures that the cover does not directly contact the surgical intervention site 53. The transparent cover as seen in FIG. 3 permits the clinician to continuously view the surgical intervention site while maintaining the surgical intervention site 53 in an aseptic condition. An adhesive layer 66 is provided, and which is applied in a given pattern on the second surface 64. This adhesive layer 66 is operable to adhesively attach the cover 60 in covering relation relative to the aperture 45 by adhering the cover to the area of the first portion 44 which is adjacent to the aperture 45. This adhesive layer 66 has adhesive strength which is less than the adhesive strength provided by the adhesive coating 52. This permits the cover 60 to be repeatedly moved between the first and second positions 71 and 72 without pulling the first portion 44 away from the aseptic treatment site 53. The transparent cover 60 is moveable along a substantially arcuately path of travel indicated by the numeral 70. The path of travel is defined between a first position 71 wherein the transparent cover is disposed in substantially covering relation relative to the aperture (FIG. 4), and a second position 72 wherein the transparent cover 60 allows access to the aseptic treatment site.

OPERATION

The operation of the described embodiment of the present is believed to be readily apparent and is briefly summarized at this point.

The present invention relates to a covering for an aseptic treatment site 10 and is best understood by FIG. 2 and following. As shown therein, the invention includes a substrate defining a first portion 44 which permits selective access to an aseptic treatment site on a patient and which defines an aperture 45; and a transparent cover 60 is borne by the substrate and which is removably affixed in substantially aseptic covering relation relative to the aperture 45. More particularly, the present invention 10 relates to a covering for an aseptic treatment site 53 which includes a flexible substrate defining a first portion 44, having opposite first and second surfaces 50 and 51, and which defines an aperture 45 which permits access to an aseptic treatment site 53 on the patient. Still further, a first adhesive region 52 is borne on the second surface of the flexible substrate defining the first portion 44, and which substantially surrounds the aperture 45. A flexible transparent cover 60 is moveably affixed on the first surface 50 of the first portion 44, and which is moveable along a course of travel 70 between a first, covering position 71 relative to the aperture 45, and which permits observation of the aseptic treatment site 53, to a second, uncovered position relative to the aperture, and which permits access to the aseptic treatment site. Further, a second adhesive region 66 is borne by the flexible, transparent cover, and which releasably adhesively affixes the flexible transparent cover to the first surface 50 of the flexible substrate defining the first portion.

In the present invention, a covering for an aseptic treatment site 10 includes a flexible substrate defining a main body 30, having a first region 41, and a releasably detachable second region 42. The first region defines an aperture 45 which permits access to an aseptic treatment site on a patient 53. A first adhesive region 52 substantially surrounding the aperture 45, and is borne by the first region. The first adhesive region releasably adhesively affixes the first region 41 on the body of the patient in an orientation such that the first region surrounds the aseptic treatment site 53. A flexible transparent cover 60 is provided and hingedly affixed on the first surface 50 of the flexible substrate. The transparent cover has a peripheral edge, opposite first and second surfaces 63 and 64, and opposite first and second ends 61 and 62. As seen in the drawings, the second end 62 of the flexible transparent cover 60 is hingedly affixed on the first surface 50. The first end 61 is moveable along a substantially arcuately shaped path of travel 70 between a first position 71, wherein the transparent cover 60 is disposed in covering relation relative to the aperture 45, and substantially out of direct contact with the aseptic treatment site 53, to a second position 72, wherein the transparent cover 60 is disposed in an orientation which allows access to the aseptic treatment site 53 by way of the aperture 45. A second adhesive region 66 is disposed on either one of the transparent cover 60 or the first region 41 and which releaseably adhesively affixes the transparent cover on the substrate and in the first covering position 71 relative to the aperture 45. The second adhesive region releases the transparent cover from the first position when force is applied to the first end 61 of the transparent cover. The second adhesive region permits the transparent cover to be repeatedly moved between the first and second positions 71 and 72 without substantially adhesively detaching the first adhesive region 52 from the patient.

Therefore it will be seen that the present invention provides many advantages over the prior art surgical drapes which have been utilized heretofore inasmuch as a clinician may maintain an aseptic treatment site long after a patient has been removed from a surgical theater by merely detaching the second region 42 from the first region 41, and thereafter observing the surgical intervention site through the transparent cover 60. In the event that further intervention is required by the clinician, the patient may be moved back into a surgical theater and intervention may commence by removing the transparent cover without need for further aseptic treatment of the site.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A covering for an aseptic treatment site comprising:
   a substrate defining a fenestration which permits selective access to an aseptic treatment site on a patient; and
   a transparent cover removably affixed to a surface of the substrate in substantially aseptic covering relation relative to the fenestration, said transparent cover defining a cavity over the aseptic treatment site when the transparent cover is disposed in covering relation relative to the fenestration, said cavity representing an empty space bound by (i) a lower surface of the transparent cover spaced away from and above the aseptic treatment site, (ii) a peripheral edge of the substrate along walls of the fenestration, and (iii) an upper surface of the aseptic treatment site on the patient;
   wherein the substrate comprises a first region having a first region outer periphery, and a selectively detachable second region joined to the first region along the first region outer periphery, said transparent cover being positioned completely within the first region outer periphery.

2. A covering as claimed in claim 1, wherein the selectively detachable second region comprises a disposable sterile drape.

3. A covering as claimed in claim 2, wherein a plurality of weakened areas surrounds the first region so as to facilitate detachment of the second region from the first region.

4. A covering as claimed in claim 3, wherein the second region is fabricated from a cellulosic substrate, and the weakened areas are perforations formed in the cellulosic substrate and which define the periphery of the first region, and wherein the plurality of perforations permits the second region to be removed from the first region by tearing the cellulosic substrate along the perforations.

5. A covering as claimed in claim 1, wherein the first region has a first portion which defines the fenestration, and a second portion which is made integral with the first portion, and wherein the second region is selectively detachable relative to the second portion.

6. A covering as claimed in claim 5, wherein the first portion has a first surface and an opposite second surface, and wherein the first surface is juxtaposed relative to the transparent cover when the transparent cover is disposed in substantially aseptic covering relation relative to the fenestration, and wherein the second surface has an adhesive coating applied thereto and which releasably adhesively secures the first portion to the patient in a fixed location relative to the aseptic treatment site.

7. A covering as claimed in claim 5, wherein the transparent cover is hingedly mounted on the first portion, and is moveable along a substantially arcuately shaped path of travel between (i) a first covering position, wherein the transparent cover is disposed in substantially aseptic covering relation relative to the fenestration, and (ii) a second uncovered position wherein the transparent cover allows access to the aseptic treatment site.

8. A covering as claimed in claim 1, further comprising an adhesive applied to an upper surface of the covering and disposed in a location which is adjacent to the fenestration, and wherein the adhesive releasably secures the transparent cover in substantially aseptic covering relation relative to the fenestration.

9. A covering as claimed in claim 1, and further comprising a pattern of adhesive on a lower surface of the transparent cover and which is operatively adapted to releasably secure the transparent cover in substantially aseptic covering relation relative to the fenestration.

10. A covering as claimed in claim 9, wherein said pattern of adhesive comprises a line of adhesive that surrounds the fenestration when the transparent cover is positioned in covering relation relative to the fenestration, and wherein a portion of the lower surface of the transparent cover that extends over the fenestration is free of adhesive.

11. A covering for an aseptic treatment site, comprising:
 a flexible substrate having opposite first and second surfaces, and which defines a fenestration which permits access to an aseptic treatment site on a patient;
 a first adhesive region borne on the second surface of the flexible substrate, and which substantially surrounds the fenestration; and
 a flexible transparent cover hingedly affixed on the first surface of the flexible substrate, and which is repeatably moveable along a course of travel between (i) a first, covering position relative to the fenestration which permits observation of the aseptic treatment site, to (ii) a second, uncovered position relative to the fenestration which permits access to the aseptic treatment site, and (iii) back to the first, covering position without contacting an area bound by the fenestration.

12. A covering as claimed in claim 11, and wherein the flexible substrate comprises first and second regions, with the flexible transparent cover being positioned completely within the first region, and wherein the first region may be selectively detached from the second region.

13. A covering as claimed in claim 12, wherein the first region comprises first and second portions with the first portion defining the fenestration, and wherein the second portion may be selectively detached from the second region.

14. A covering as claimed in claim 12, wherein a plurality of weakened areas are formed in the substrate so as to surround the first region, and wherein the first region is detachable from the second region by tearing the substrate along the plurality of weakened areas.

15. A covering as claimed in claim 11, further comprising a second adhesive region borne by the flexible, transparent cover, and which releasably adhesively affixes the flexible transparent cover to the first surface of the flexible substrate when the flexible transparent cover is in the first, covering position.

16. A covering as claimed in claim 15, and wherein the first adhesive region affixes the flexible substrate on the patient and in substantially sealing relation about the aseptic treatment site, and wherein the first adhesive region has a first adhesive strength, and wherein the second adhesive region has a second adhesive strength which is less than the first adhesive strength.

17. A covering as claimed in claim 15, and wherein the first adhesive region releasably affixes the flexible substrate on the patient, and wherein the second adhesive region releasably affixes the transparent cover in covering relation relative to the fenestration, and further allows the transparent cover to be repeatedly moved from (i) the first, covering position relative to the fenestration, to (ii) the second, uncovered position and back to (i), without adhesively detaching the first adhesive region from the patient.

18. A covering for an aseptic treatment site comprising:
 a substrate defining a fenestration which permits selective access to an aseptic treatment site on a patient; and
 a transparent cover which is releasably adhesively affixed to the substrate and positioned in covering relation relative to the fenestration, said transparent cover having an upper surface and a lower surface, said lower surface having a pattern of adhesive thereon for releasably adhesively affixing the transparent cover to the substrate, wherein a portion of the lower surface of the transparent cover that extends over the fenestration is free of adhesive,
 wherein the substrate comprises a first region having a first region outer periphery, and a selectively detachable second region joined to the first region along the first region outer periphery, said transparent cover being positioned completely within the first region outer periphery.

19. A covering as claimed in claim 18, wherein said pattern of adhesive comprises a line of adhesive that surrounds the fenestration when the transparent cover is positioned in covering relation relative to the fenestration.

20. A covering for an aseptic treatment site comprising:
 a first region of a substrate having opposite first and second surfaces, the first region defining a fenestration which permits access to and surrounds a treatment site on a patient;
 a layer of adhesive borne by the second surface of the first region, the layer of adhesive being operatively adapted so as to adhere the first region in a substantially fixed location relative to the treatment site;
 a second region of the substrate which is releasably attached to and surrounds the first region, wherein the second region is detachable from the first region so as to leave the first region on the patient and around the treatment site; and a transparent cover which is affixed to the first surface of the first region and positioned completely within the first region in covering relation relative to the fenestration, the transparent cover allowing medical personal to view the treatment site without removing the transparent cover and while maintaining the treatment site in an aseptic condition.

21. A covering as claimed in claim 20, wherein a line of perforations separates the first region and the second region so as to facilitate detachment of the second region from the first region.

22. A covering as claimed in claim 20, wherein the transparent cover defines a cavity over the treatment site when the transparent cover is disposed in covering relation relative to the fenestration such that no portion of the covering comes into contact with the patient within an area bound by the fenestration.

23. A disposable drape comprising:
a first region comprising first region material having a first region outer periphery and a fenestration positioned within the first region outer periphery and surrounded by the first region material, wherein the fenestration is sized so as to surround an aseptic treatment site on a patient so that the aseptic treatment site is viewable and accessible through the fenestration; and
a second region surrounding the first region outer periphery of the first region, said second region being detachably joined to the first region material such that detachment of the second region from the first region does not alter an outer periphery of the fenestration.

24. A drape as claimed in claim 23, wherein the first region and the second region are separated from one another by a plurality of weakened areas that form a pattern of perforations.

25. A drape as claimed in claim 23, further comprising a transparent cover having a transparent cover outer periphery, said transparent cover being removably affixed to the first region in a substantially aseptic covering relation relative to the fenestration such that the transparent cover outer periphery surrounds the fenestration when the transparent cover is in a first, covering position relative to the fenestration.

26. A drape as claimed in claim 25, wherein said transparent cover adhesively attaches to the first region in a substantially aseptic covering relation relative to the fenestration.

27. A drape as claimed in claim 23, further comprising an adhesive on a back side of the first region material for releasably adhering the first region material to a patient, said adhesive surrounding the fenestration.

28. A method of covering an aseptic treatment site, said method comprising the steps of:
positioning the disposable drape of claim 23 over the aseptic treatment site such that the aseptic treatment site is accessible through the fenestration;
covering the aseptic treatment site with a transparent cover so as to releasably affix the transparent cover to areas of the first region surrounding the fenestration; and
detaching the second region from the first region.

29. A method as claimed in claim 28, further comprising:
after said positioning step and prior to said covering step, performing a surgical procedure on the aseptic treatment site.

* * * * *